United States Patent
Nabarro et al.

(10) Patent No.: US 6,869,406 B1
(45) Date of Patent: Mar. 22, 2005

(54) MEASURING DEVICE AND METHOD

(75) Inventors: Daniel Joseph Nunes Nabarro, London (GB); Alun Wilcox, Richmond (GB); Timothy Roland Manson, London (GB); Julian Francis Ralph Swan, London (GB)

(73) Assignee: T-Bra Limited (GB)

(*) Notice: Subject to any disclaimer, the term of this patent is extended or adjusted under 35 U.S.C. 154(b) by 177 days.

(21) Appl. No.: 10/110,793

(22) PCT Filed: Oct. 18, 2000

(86) PCT No.: PCT/GB00/03999

§ 371 (c)(1),
(2), (4) Date: Jul. 18, 2002

(87) PCT Pub. No.: WO01/28375

PCT Pub. Date: Apr. 26, 2001

(30) Foreign Application Priority Data

Oct. 18, 1999 (GB) .............................................. 9924618
Jul. 4, 2000 (GB) .............................................. 0016464

(51) Int. Cl.[7] .............................................. A61B 5/103
(52) U.S. Cl. ...................................... 600/587; 73/149
(58) Field of Search .......................... 600/587; 33/512; 623/7; 73/149

(56) References Cited

U.S. PATENT DOCUMENTS

| 2,559,501 A | 7/1951 | Graf |
| 2,725,633 A | 12/1955 | Graf |
| 4,024,856 A | 5/1977 | Kirianoff |
| 4,338,953 A | * 7/1982 | Ward .......................... 600/587 |
| 4,734,078 A | * 3/1988 | Moreau ........................ 450/38 |
| 5,414,943 A | * 5/1995 | Vogt .............................. 33/512 |
| 5,769,779 A | 6/1998 | Alderson |
| 5,965,809 A | * 10/1999 | Pechter ......................... 73/149 |
| 6,336,839 B1 | * 1/2002 | Valli .............................. 450/1 |

FOREIGN PATENT DOCUMENTS

| FR | 2 520 999 A | 8/1983 |
| GB | 2 044 470 A | 10/1980 |
| GB | 2 201 579 A | 9/1988 |

* cited by examiner

Primary Examiner—Eric F. Winakur
(74) Attorney, Agent, or Firm—Stevens & Showalter LLP

(57) ABSTRACT

A method of and system for buying or selling bras involves establishing a database of bras containing bra characteristic data including bra size and bra cup size measured from a sample of actual bras; measuring a wearer's breast and torso size to obtain wearer characteristic data; searching the database to find bra characteristic data within the database matching the wearer characteristic data; and listing for selection by the wearer any bras in the database whose characteristics match the wearer characteristic data. Apparatuses and methods for measuring breast characteristics and bra characteristics are also disclosed, the former involving application of a receptacle to the breast and the latter involving expansion of bladders within the cups of a bra, the aim in both cases being to establish volumetric data for the purposes of correlation using the database.

38 Claims, 8 Drawing Sheets

MEASURING DEVICE AND METHOD

BACKGROUND OF THE INVENTION

The present invention relates to a device and method of self-measurement for the fitting of bras. More generally the invention encompasses improvements relating to the sale, fitting and purchase of bras and measurement of bras, as well as related quality assurance techniques relating to bras.

In this specification the term 'bra' will be used conveniently to encompass all clothing designed closely to fit a wearer's breasts, thus including other forms of lingerie such as body suits, as well as swimwear and other sportswear such as leotards.

Bra fitting is bedevilled by variations in size, shape and disposition of the breasts, by the amorphous nature of the breasts themselves, and by the fact that many women are never measured for bra size, either professionally or otherwise. Nevertheless, when buying a bra, most women know from previous experience roughly the size that is required. This is always an approximation as changes occur to the size and shape of breasts at different times during the menstrual cycle and as the years progress. Also, substantial and often irreversible changes in breast size and shape can occur during and after pregnancy.

A typical way to chose a bra is either by choosing a favourite style or make, regardless of the accuracy of the fit, or to try on a selection of styles in a range of sizes and makes. In this way, best fit is ascertained by trail and error. Both processes take time, are dependent on available stock and do not always result in the purchase of a properly fitting bra. Often, when looking for a particular style, the style will have been discontinued or the appropriate size is out of stock. In this case, the consumer must resort to trial and error of other styles and/or makes or return to the retail outlet at a later date.

When choosing bras from mail order catalogues or via the Internet, the option of trying a bra for fit is much more restricted since, if the bra does not fit, it must be returned to the provider, usually by mail, and another choice made. If the consumer is unsure of the size she requires, it could take several attempts and much time and frustration before an appropriate bra is found. Alternatively, the consumer may order more than one bra with a view to returning the ones that are incorrect. This process wastes resources, especially for the retailer, who may have to repackage and redistribute the returned items.

The quest to find a correct fitting bra is further compounded by the problem that a lot of women fall in between available standard sizes and that the so-called standard sizes are not uniform between different makes and styles of bras. For example, a 34B bra supplied by one maker may provide an adequate fit in a particular style. However, a 34B in a similar style made by a different maker may provide a different, perhaps less good, fit.

The composition of a bra, such as its elastane or Lycra® content, together with additional features such as underwires, padding etc., also affect the fit of a bra and must be taken into account when choosing the correct size.

For women who are unsure of their size, some retail outlets provide a bra measuring service whereby measurements are taken either with or without a bra being worn. Apart from the advantage of obtaining expert advice or at least a second opinion as to fit, professional measuring services have many drawbacks. For example, if the measurement is taken with a bra on, there is the advantage that the breasts are supported but the resulting measurement may be inaccurate if the bra is not an accurate fit to start with. If the measurement is taken without a bra being worn, the measurement will also be inaccurate since the breasts are unsupported and therefore are of a different shape and volume compared to when they are supported.

The significance of support is that a breast is largely constituted of fatty tissue having a resiliently compressible, gelatinous consistency whose shape and volume will adapt to some extent to suit a receptacle such as a bra cup in which the breast is contained. When there is no such support, gravity will change both the shape and volume of the breast, obviously with increasing effect the greater the size and weight of the breast.

Even a professional measuring service is not immune from the drawback that the accuracy of breast and torso measurement for fitting a bra will usually depend on the level of training and experience of the person doing the measuring. It is also true that bra-fitting experts apply an element of subjectivity to their work. The aim of such experts is not to arrive at a universal bra size measurement that the user can apply with confidence to bras in general, but instead to fit the consumer to one of the bras available in stock, the purpose of measurement therefore being to select a limited range of bras that the user can try on and select from. As noted above, such trial and error is all well and good in a store environment if the consumer has the time and inclination to visit the store, but it does not suit the mail order and Internet shopping methods that many consumers increasingly prefer.

A further problem with professional measuring services is that many women feel uncomfortable about being measured in a semi-naked state by a stranger. As a result, the measurement/fitting may be hurried and incorrect advice given.

Self-measuring guides are therefore available. These generally involve measuring the circumference of the torso under the breasts to obtain a torso measurement, followed by taking a measurement across the breasts at the largest point, i.e. across the nipples in an 'over-bust' measurement. Then, these measurements are put into a formula to work out a nominal torso and bra cup size. The bra cup size is related to torso size and also to the difference between torso size and over-bust measurement. In other words, the difference between torso size and over-bust measurement imputes a cup size for a given torso size. However, the product of the formula is only as good as the measurements that are put into the formula, and unfortunately those measurements are often inaccurate.

For example, as noted above, a certain level of expertise is required to achieve any degree of accuracy; one could hardly expect an inexpert woman, usually working on her own, to match the accuracy of measurement of an experienced bra-fitter. In particular, it is difficult to be sure that a measuring tape is held at an appropriate tension and in the correct position, which is especially difficult to ascertain across the back, either with or without the aid of a mirror. Also, the cross-nipple or over-bust measurement introduces an inherent inaccuracy because it does not take proper account of the effect of the varying depth and width of the cleavage between the breasts. The measuring tape bridges the cleavage rather than following the contour, and so cannot accurately tell if a particular apparent breast size is due to the degree of separation and protrusion of the breasts rather than the overall breast size.

Furthermore, the final measurement will be dependent on the type of bra being worn, it being noted that measurement often takes place while wearing a bra and that different bras impose different shapes upon the breasts that they support. A particular source of inaccuracy arises where the bra is designed to flatten the breast or maximise cleavage because such distortion of the breasts gives a misleading over-bust measurement. In general, there is a tendency to overestimate torso size and to underestimate over-bust measurement: as cup size is imputed from the difference between those measurements and with regard to the torso size, the combination or sum of errors in these critical measurements magnifies errors in apparent cup size.

Consequently, many women wear ill-fitting-bras that are uncomfortable and provide insufficient support, which has adverse effects on posture and shape in later years. The correct fitting of a bra is especially important while breasts are developing during the teenage years and incorrect fitting during this time can lead to complications in later years.

The problems outlined above have been recognised for some years and various attempts have been made to invent devices to overcome these problems. For example. GB 2201579 (Sutherland) describes a measurement and fitting harness set for determining cup size and (optionally) other sizes or fittings for a production line or made-to-order bra. The harness has two breast-receiving cups, adjustable body and neck support straps and adjustable spacing between the cups. It is provided that at least one cup should differ in size by a predetermined measurement from other cups of other pairs. The unit size of the cups is based on units of maximum width at the widest part of the breast-receiving cup, providing a series of discrete sizes.

The user is provided with a set of eight harnesses for self-measurement whereby the correct cup size is selected by trial, i.e. the measuring technique described is akin to trying on a range of sizes in a retail outlet. An advantage of the measuring device described is that the breasts are measured in a supported state. However, since the sizing of the cups is dictated by the sizing provided by the harness, this does not provide an accurate measurement of breast size or overcome the problem of non-uniformity between the sizes of different makes and styles of bras. Therefore, the measurement obtained from the device may only be used to provide a rough estimate of size around which the consumer should look for an appropriately fitting bra. It follows that the consumer must still go through the process of trial and error to find a bra that fits correctly.

It is also apparent that the harness set of GB 2201579 is very complex to manufacture and to use, and would be prohibitively expensive for occasional or one-off use.

GB 1468762, also in the name of Sutherland, describes a harness for ascertaining torso and strap measurements as well as the separation between the two breasts. The cup size is fixed and specified by the user so that a suitable harness can be supplied. Measurement indicia are provided by a series of numbered hooks and eyes or interlocking slotted tape measures.

In order, for example, to measure accurately the length of shoulder strap required, the user must fiddle with small hooks and eyes behind her back. Unless the numerical indicia are sufficiently large, it can fairly be assumed that the scale is not readily visible and that it would be difficult to obtain an accurate measurement without much fiddling and possibly the help of a second person.

FR 2520999 to Dessapt describes a device for determining breast volume for patients requiring prosthesis or surgical enlargement. The device allows the surgeon to obtain accurate information on the required volume before carrying out surgery, and enables the patient to appreciate the likely result beforehand, as well as participating in the decision regarding size. The device includes cups of differing volumes, which can be interchangeably attached to the same harness.

The measurement provided by this device is a volumetric measurement which provides information on how much material is required to fill a selected volume, rather than how best to support the volume.

U.S. Pat. No. 5,485,855 (Shiraiwa) describes a measuring device for measuring breast shape. Measurements are taken from the base of the breast to the nipple, and the horizontal width of the breast across the nipple, by means of two tape measures mounted on a curved base member which is located underneath the breast in use. The sum of the values provided by the two tape measures can be used to select an appropriate cup size and shape. The device is also designed so that it can be mailed to the user, as well as for use in shops.

A major drawback with this device is that the breast is measured in the unsupported shape which, as outlined above, is far from ideal.

Even if a breast is supported during measurement, the way in which the breast is supported can introduce substantial inaccuracies. A prime example of this problem is evident from GB 2044470 which discloses calibrated receptacles for measuring breast volume. The receptacles are formed by bending or rolling flat sheets of clear plastics and two receptacle shapes are suggested, one being rolled from a circular sheet to form a cone-shaped receptacle and the other being rolled from an oblong sheet to form a tubular receptacle. The user then forces her breast into the receptacle while holding the receptacle against its own resilience to prevent it unfurling back into a flat sheet. The volume of the breast within the receptacle is read off by measuring the circumference of the base of the cone or, in the oblong-sheet tubular embodiment, by measuring the position of a piston within the tube.

The main problem in prior art such as GB 2044470 is that the user has to force her breast into the receptacle to cram the breast into every corner of the receptacle, this being the only way of filling the receptacle to measure breast volume. The oblong-sheet tubular embodiment even requires the user to press the piston into the end of the tube against the front of the breast. So, the circular-sheet, conical embodiment measures the volume of a conical, highly-compressed breast whereas the oblong-sheet, tubular embodiment measures the volume of a flat-fronted cylindrical highly-compressed breast. Such is the degree of compression necessary to contort the breast into the receptacle that the volume of the breast reduces to an extent that completely undermines its purported volumetric measurement.

Another problem of prior art such as GB 2044470 is that the edge of the receptacle closest to the user's torso in use is planar. So, the receptacle does not fit snugly against the curvature of the user's torso around the breast unless it is pressed uncomfortably into the user's flesh.

Finally, U.S. Pat. No. 4,454,409 (Sehres) discloses a bra-size calculator whose aim is to provide a convenient means for calculating bra and bra cup sizes based on measurements typically used by professional bra-fitters. This document is interesting largely to illustrate that the complexity of self-measurement has created the need for such a device, and for its more detailed discussion of existing professional bra-fitting techniques. There is also a particularly revealing tale in the introduction concerning two hundred women who thought that they were bra size 34B, but only two of whom when measured actually turned out to be that size.

Nevertheless, the bra-size calculator of U.S. Pat. No. 4,454,409 does nothing to facilitate accurate measurement and so suffers the problem of all non-intelligent calculating or computing devices, colloquially referred to as 'garbage in, garbage out': a bra-size calculator provided with the wrong measurements will unerringly produce the wrong bra fitting. Even if, against all odds, a user accurately makes all three measurements required by the calculator, enters those measurements correctly and then uses the calculator properly to produce a nominally correct result, fundamental problems remain. These are that the measurements themselves are not taken directly from the breast—breast size is merely inferred from other measurements—and there is no guarantee that a nominally matching bra will actually match the measured bra size.

It is against this background that the present invention has been made. The invention aims to provide an accurate measurement of breasts and bras which facilitates the selection of the correct bra size and style to suit an individual's requirements. Put simply, an objective of the invention is to recommend to a user a range of bras that will fit, not a range of bras of a given nominal size that may or may not fit.

SUMMARY OF THE INVENTION

From one aspect, the invention resides in a breast measuring method comprising applying a receptacle of known volume to a breast to determine the volume of the breast when the breast is comfortably fitted within and supported by the receptacle, fit being checked by observing the breast through the receptacle, the receptacle being pre-formed to be substantially of pear-shaped, teardrop or cardioid vertical section emulating the shape of a bra-supported breast and being sufficiently rigid to be self-supporting and to support the breast in the shape of the receptacle.

The method can be performed first on one breast and then on the other breast or on both breasts simultaneously. In the latter case, two receptacles can be linked and is applied together to the respective breasts, and torso girth can be measured by passing a tape or strap around the torso and reading a girth measurement from indicia on the tape or strap situated at the front or side of the torso. For accurate and consistent measurement, a predetermined tensile load is preferably applied to the tape or strap before reading the girth measurement.

The breast measuring method can be effected by using a breast measuring apparatus comprising a receptacle of known volume applicable to a breast to check for comfortable fit and to determine the volume of the breast comfortably fitted within the receptacle, the receptacle being pre-formed to be substantially of pear-shaped, teardrop or cardioid vertical section emulating the shape of a bra-supported breast and being sufficiently rigid to be self-supporting and to support the breast in the shape of the receptacle, a wall of the receptacle being transparent or translucent to enable fit to be checked by observing the breast through the receptacle.

The user is preferably provided with a set of such receptacles of different volumes and/or shapes, each receptacle of the set including indicia indicating its volume and/or shape. As aforesaid, a pair of receptacles can be linked to emulate a bra, in which case a torso strap and optionally also shoulder straps can be provided.

In a related aspect, the invention resides in a method of buying or selling bras as herein defined. The method comprises establishing a database of bras containing bra characteristic data including bra size and bra cup size measured from a sample of actual bras; measuring a wearer's breast and torso size to obtain wearer characteristic data; searching the database to find bra characteristic data within the database matching the wearer characteristic data; and listing for selection by the wearer any bras in the database whose characteristics match the wearer characteristic data.

The bra characteristic data preferably includes bra cup shape data, in which case the method further comprises measuring a wearer's breast shape and including the wearer's breast shape in the wearer characteristic data. For a consistent, repeatable and objective assessment of size and fit, it is preferred that the bra cup size and wearer breast size are measured volumetrically and moreover that the volumetric is measurement of the wearer breast size is performed when the breast is in a supported shape.

To cater for wearer preference, the bra characteristic data advantageously includes bra type and/or bra features data, and the method further comprises including wearer preference data as to bra type and/or bra features in the wearer characteristic data.

This aspect of the invention extends to a system for buying or selling bras as herein defined, the system comprising a database of bras containing bra characteristic data including bra size and bra cup size measured from a sample of actual bras; measuring means for measuring a wearer's breast and torso size to obtain wearer characteristic data; search means for searching the database to find bra characteristic data within the database matching the wearer characteristic data, and selection means for listing for selection by the wearer any available bras in the database that match the wearer characteristic data.

The flexibility of this system lends itself to use in retail outlets as well as the selection of bras by mail order and the Internet. Indeed, the invention may be the key to wider public acceptance of bra shopping via mail order or the Internet.

A bra measuring apparatus that can be employed in conjunction with the invention for measuring a bra as herein defined comprises at least one bladder expandable under internal fluid pressure within a cup of a bra thus supported, and measurement means for measuring the volume and/or pressure of the fluid within the bladder when the cup of the bra has been filled.

The support means is suitably shaped to emulate a torso and can be divided into segments so that adjustment means can adjust separation between the segments and hence the girth of the artificial torso. First and second bladders are preferably situated on respective segments, the or each bladder is shaped to emulate a breast, and the or each bladder is interchangeable with bladders of different sizes and/or shapes.

The measurement means preferably includes a volumetric scale adapted to measure the volume of fluid delivered to the or each bladder and may also include a pressure sensor in communication with the or each bladder. A detector associated with this pressure sensor can detect a discontinuity in pressure rise when the cup of the bra is filled by the bladder, whereupon means associated with the detector suitably stops expansion of the bladder.

Surface pressure sensors can be associated with the support means, and stress sensors can be associated with the bra.

The corresponding bra measuring method comprises supporting a bra, expanding a bladder under internal fluid pressure until a cup of the bra thus supported has been filled, and measuring the volume and/or pressure of the fluid within the bladder that fills the cup. This method advantageously further comprises observing fit on a support means supporting the bra, for example by observing deflection of a support surface of the support means and/or by observing any gap between the cup and the support means.

A plurality of nominally identical bras can be measured to determine manufacturing tolerance, this method suitably comprising selecting a random sample of bras from a bra production facility, measuring the bras of that sample, and feeding back tolerance information to that facility.

The invention may also be used in conjunction with a measuring strap or tape for use around a user's torso, the strap or tape comprising a tension-indicating means having first and second portions that are linked by a resilient bias means for relative movement when the strap or tape is under longitudinal tension, wherein the resilient bias means acts against the longitudinal tension and the portions include co-operable indicia that are brought into mutual alignment by said relative movement at a predetermined longitudinal tension.

Conveniently, the first and second portions are strap or tape portions that define a mutual longitudinal axis and are disposed generally end to end along that axis, and the first and second portions overlap in the region of the indicia. The first portion can include a window or cut-out and the second portion can include an indicator aligned with and visible through that window or cut-out when the strap or tape is at the predetermined longitudinal tension. The indicator is preferably at least partially hidden by the first portion when the strap or tape is not at the predetermined longitudinal tension.

The strap or tape can be used in a method of measuring the girth of a torso or other compressible body, comprising passing the measuring tape or strap around the body, applying a predetermined tension to the tape or strap by reading a tension indicator associated therewith, and measuring the girth of the body while maintaining said predetermined tension. The predetermined tension can be maintained by fastening the tape or strap to itself or to another structure.

BRIEF DESCRIPTION OF THE DRAWINGS

In order that the invention may be more easily understood, reference will now be made, by way of example, to the accompanying drawings, in which:

FIG. 7 showing the device without a bra and FIG. 8 showing the device with a bra that is being measured;

DETAILED DESCRIPTION OF THE INVENTION

Figure 1:
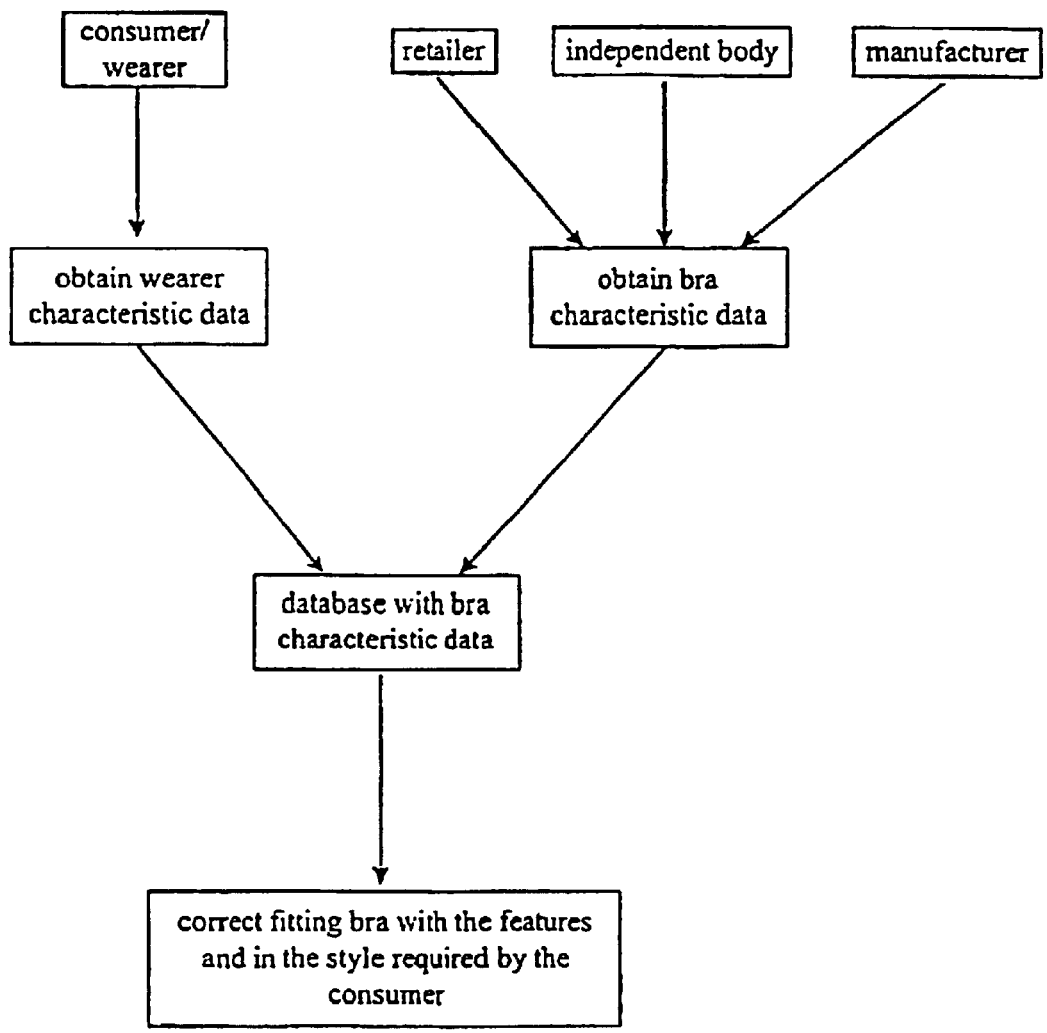
FIG. 1 is a schematic diagram illustrating the correlation of two volumetric measurements to provide information on a suitable bra.

Referring firstly to FIG. 1, an aspect of the invention relates to the correlation of breast volume with bra volume, by obtaining a volumetric measurement of each breast which is correlated to volumetric measurements of bras. In this way, the two measurements are matched so that the user is provided with a correctly fitting bra thus eliminating the need for trial and error of a range of bras, incorrect fitting and consequential discomfort. A further advantage of matching two accurate volumetric measurements is that the inevitable discrepancy between different styles and makes of bras is mitigated.

In FIG. 1, an accurate volumetric measurement of actual bra cups is obtained by a retailer, a manufacturer or preferably an independent body such as a measuring laboratory. In order to provide the consumer with the maximum amount of information so as to give a wide and informed choice—and also to confer statistical validity upon the measurement findings—it is necessary that volumetric measurements are obtained for as many styles, sizes and makes of bra as possible. This information is held on a database to which a consumer has access, in the manner of a look-up table.

Advantageously, several nominally identical examples of a given bra are measured in this way, thereby to gain an understanding of typical size tolerance for that type of bra. That information is also fed into the database. For example, some bra manufacturers may employ a greater degree of manual labour than others, and this can be expected to show in a wider size tolerance range that should be taken into account when selecting a bra made by that manufacturer. Suitably, random samples are taken from a production line, and feedback concerning tolerance is sent back to the manufacturer for quality assurance purposes.

By means such as the shaped bladders that will be described below with reference to the bra measuring device of FIGS. 7 and 8, the cup shape characteristics of a bra are also measurable. If measured, these cup shape characteristics can be added to the database for correlation with breast shape characteristics measured by a user.

In parallel and in accordance with another aspect of the invention that will be discussed more thoroughly below in relation to FIGS. 2 to 6, the consumer obtains an accurate volumetric measurement of her breasts, and torso circumference or girth. This measurement is then queried on the database by means of a search engine, which matches the measured volume, and optionally also the shape, of the consumer's breasts with the volumes and, if appropriate, shapes of suitably-sized bras held on the database. Once a match is obtained, the search engine will inform the consumer of any matches by suggesting at least one style and/or make of bra that would provide a suitable fit. It is preferred that the search engine applies fuzzy logic so as intelligently to match the available bras to the user's requirements, having regard to issues such as manufacturing tolerance.

As many consumers will require specific types of br the search engine includes the option of adding in features of preference as to style and function, such as padding or underwiring, or sports, maternity or lacy, which will reduce the number of results produced. This is a standard facility of most search engines. To this end, the database of bra characteristics also includes classification fields enabling selection of bras that match the options selected by the consumer.

The addition of some features, especially padding for example, may markedly alter the size of the bra required. However, if the volume of such a bra is known and is correlated with an accurate measurement of breast volume, the consumer will immediately be able to ascertain the correct size that she requires.

Further to help the consumer, the information held on bra characteristics may also include information as to where the consumer can locate the correct bra, or, if the information is held by a retailer, whether or not the bra selected is in stock. If the bra is not in stock, the consumer may then be prompted to try a different bra which is in stock. In this way, the consumer will be advised as to the correct bra with minimum time, effort and frustration involved.

The accurate bra measurement and hence the accurate bra characteristics database of the invention provides a further useful facility. If a woman knows that she is usually comfortable in a particular size of a particular type of bra, say a 34B Wonderbra (trade mark) and typical characteristics such as size and size tolerance of such a bra are known by means of the invention, it is possible to seek matching characteristics in other types of bra within the database. Effectively, the user tells the system "I am size X in a particular bra style" and asks the system "in view of that, what size would I be in bra styles Y or Z?"

Turning to the breast measuring device in FIGS. 2 to 5 of the drawings, this aspect of the invention seeks to determine with accuracy the volume of the breast when the breast is in a supported state. The breasts are measured by one or a plurality of self-supporting receptacles that are appropriately shaped, have a known volume and are of sufficient transparency or translucency to enable the user to see how the breasts fit into the receptacles to ensure correct fitting.

In order for the user accurately to determine her breast volume, she is provided with a series of measuring receptacles in a set for self-measurement. The measuring receptacles in the set are of different sizes and shapes, covering the approximate known breast size and shape of the user. It is possible that the measuring receptacles could be used in retail outlets to enable customers to measure themselves before selecting an appropriate bra. However, it is particularly envisaged that a customer to would request a set of measuring receptacles to be sent to her by mail so that she may measure herself in the privacy of her own home.

To accommodate mailing, the receptacles are shaped so that one receptacle can be nested within another to some extent for ease of packaging. For example, the receptacles can be stacked within each other in descending volume to reduce the space required to package the set. The receptacles are also lightweight and economical to produce, to which end the receptacles are preferably moulded from lightweight plastics.

Figure 2:
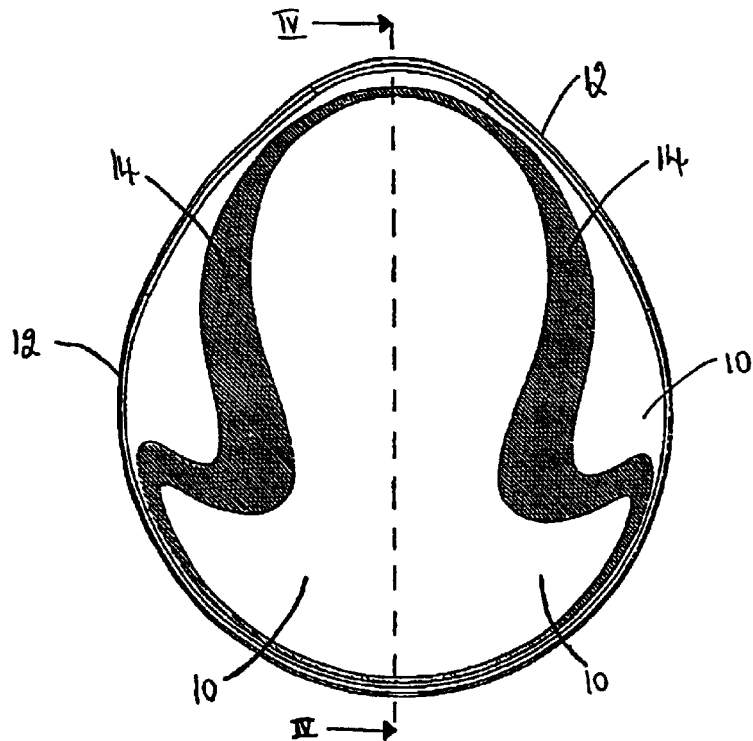
FIG. 2 is a front view of one embodiment of a single measuring receptacle.
Figure 3:
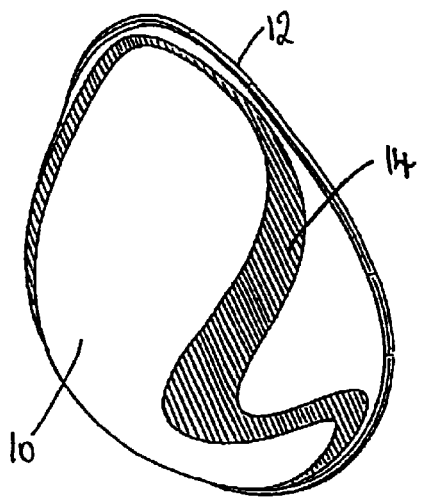
FIG. 3 is a perspective view of the embodiment shown in FIG. 2.
Figure 4:
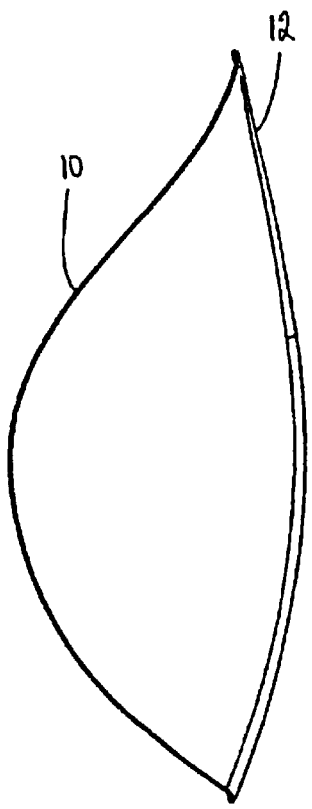
FIG. 4 is a cross-section view along line IV—IV of FIG. 2.

Referring to FIGS. 2 to 4 of the drawings, a measuring receptacle 10 of the present invention is a hollow cup having an internal shape that essentially mirrors the shape of a comfortably-supported breast, being complementary to its surface contour. As breasts of the same volume may differ substantially in shape from woman to woman, the receptacle 10 is shaped to suit the comfortably supported shape of the breast being measured, this being advantageous for comfort and accuracy.

In order to obtain an accurate measurement of the breast, it is preferred, but not essential, that the measuring receptacle 10 wholly or substantially surrounds the breast that it is intended to fit. Accordingly, the receptacle 10 is shaped to surround the whole or a substantial part of the breast. In use, the rim 12 of the receptacle fits around the circumference of the breast, the mass of which is supported within the receptacle 10. The rim 12 defining the edge of the receptacle 10 closest to the users torso in use is non-planar, the side edge portions being convex-curved and the top and bottom edge portions being concave-curved. In this way, the receptacle fits snugly against the curvature of the user's torso around the breast without having to be pressed uncomfortably into the user's flesh. The receptacle 10 is also symmetrical about its central longitudinal plane that is vertical in use (line IV—IV of FIG. 2), thus being usable on either of the user's breasts.

The measuring receptacle 10 may include shaping to accommodate the nipple (not shown), such as a hole or a protruding chamber at the appropriate position. Due allowance may be made in volumetric calculations for the effect upon volume of such shaping.

It will be appreciated that the shape of a breast varies according to its size. For example, a small breast tends towards a more circular frontal outline and hemispherical curvature compared to a larger breast which will tend towards a more ovate frontal outline and a half pear-shaped, half-teardrop or inverted semi-cardioid side: outline due to the effect of gravity. Accordingly, the circumference and shape of the measuring receptacles 10 will vary in a similar manner as breast size increases to ensure an accurate fit and measurement.

The single measuring receptacle 10 shown in frontal view in FIG. 2 is shaped to measure a breast having an approximate 36B or 36C cup measurement, according to current standard measurement terms. Accordingly, the receptacle 10 has a generally ovate frontal shape, wider towards the bottom and narrower towards the top. FIGS. 3 and 4 show the same measuring receptacle 10 viewed in perspective and longitudinal cross-section, from which it will be evident that the side outline approximates to a half teardrop, again wider at the bottom than at the top.

The volume of a breast may be ascertained by placing that breast in a single measuring receptacle 10. Depending upon the size of her breasts, the user may find it helpful to bend her torso forwards when placing a breast into the receptacle 10 so that the breast hangs down, whereupon the user lifts the receptacle 10 onto the breast. This emulates the correct way of donning a bra where the wearer's breasts are relatively large.

If the receptacle 10 is too large, the unfilled space within the receptacle 10 will be apparent because, to facilitate visualisation of the fit, the receptacle 10 has a degree of transparency or translucency so that the breast can be at least partially seen when in the receptacle 10. Similarly, if the receptacle 10 is too small, areas where the breast presses too hard against the interior of the receptacle 10 will be visible readily from the exterior of the receptacle 10 as areas of red or pink colour. In any event, if the receptacle 10 is too small, excessive pressure of the receptacle 10 on the breast will be felt and/or a gap will exist between the rim 12 of the receptacle 10 and the torso.

If the receptacle 10 selected by the user is not a suitable fit, a receptacle 10 of a larger or smaller size or different shape is selected from the set as appropriate and the procedure is repeated until a correct fit is achieved. If the receptacle 10 fits snugly is around the breast, the volume of that receptacle 10 may then be read as appropriate.

While not essential, the embodiment shown has a reinforcement around the rim 12. As best shown in the sectional view of FIG. 4, this reinforcement may be in the form of a rolled or thickened lip. However, those skilled in the art will know that other forms of reinforcement are possible. The reinforcement not only strengthens the receptacle 10 but also contributes to ensuring a snug fit around the breast.

Although not shown in FIG. 4, the reinforcement may include means to tolerate some variation in size and shape between breasts. For example, a strip of foam rubber may be fixed to the rim to provide some tolerance, as well as providing a greater degree of comfort to the user where the receptacle 10 abuts the user's torso.

When considering the material from which the receptacles 10 are made, certain criteria should be taken into account. For instance, blow moulding of polymers may be used to impart a texture to the surface of the plastic. It would also be possible to perforate the plastic to combine ventilation with texturing.

An advantageous feature evident from FIGS. 2 and 3 is a gripping surface region 14 on the outer surface of the receptacle 10 that extends around the outer surface in a waisted loop. The loop has a relatively small upper part and a relatively large lower part and narrows near the apex of the convex-curved outer surface in the region corresponding to the user's nipple. The gripping surface region 14 has a relatively rough surface compared to the surrounding surface of the receptacle 10 and may be applied to the receptacle 10 or, preferably, is moulded in to the receptacle 10, for example by a spark-eroded portion of a mould. The gripping surface region 14 helps to prevent the receptacle 10 slipping in the user's grasp during use, and it will be noted that the waisted loop shape coincides with the ideal position of the user's fingers when the user holds the receptacle 10 in place. The user is therefore encouraged to place her fingertips on the gripping surface region 14 while keeping her fingertips away from other parts of the receptacle 10, notably the rim portion around the gripping surface region 14 and the central portion within the loop of the gripping surface region 14, whose transparency or translucency is maintained to allow observation of breast fit through the receptacle 10.

Not only does the gripping surface region 14 help to prevent the receptacle 10 slipping in the user's grasp, it also helps users to orient the receptacle 10 correctly in use, for example by ensuring that the larger part of the loop is below the smaller part of the loop. Also, if distinctively shaped to suit a particular shape and size of receptacle 10, the gripping surface region 14 helps to distinguish that receptacle 10 from other differently-shaped or differently-sized receptacles 10 of a set.

The material of the receptacle 10 should also be of sufficient rigidity to be self-supporting. In other words, the material should have a certain bending modulus. Another consideration is the translucency of the material, the advantages of which are described above. The material should also be lightweight for it to be sent easily in the mail if so required. In general, it is preferred that the receptacles 10 are made from a material which has sufficient rigidity and inextensibility that the breasts are supported and held in an appropriate shape during measurement, but that has some flexibility for comfort in use.

Whilst the use of essentially solid polymers has been suggested above, the breast-receiving portion of the receptacle 10 could incorporate a mesh or a woven, knitted or randomly-oriented filamentary or fibrous material that has sufficient strength to hold a breast in a supported state. In this way, the receptacle 10 could be pressed flat for mailing and pressed back into shape for use, as could suitable solid polymers. Mesh and the like also has a measure of translucency even if the elements or filaments making up the mesh are themselves opaque.

In order for the user to know the volume of her breast(s), an indication of the volume of the measuring receptacle 10 is shown on the receptacle 10, either in the form of indicia or a scale which may be correlated to a look up table. For example, a certain volume or range of volumes may be assigned a particular colour or icon, so that a given volume of say 300 millilitres relates to a particular colour or icon applied to the receptacle 10. A measuring receptacle 10 may also be marked with indicia representative of the shape of the receptacle 10. Conveniently, as mentioned above, the shape of the gripping region 14 itself serves as an indication of shape and size of the receptacle 10 to which it is applied.

Figure 5:
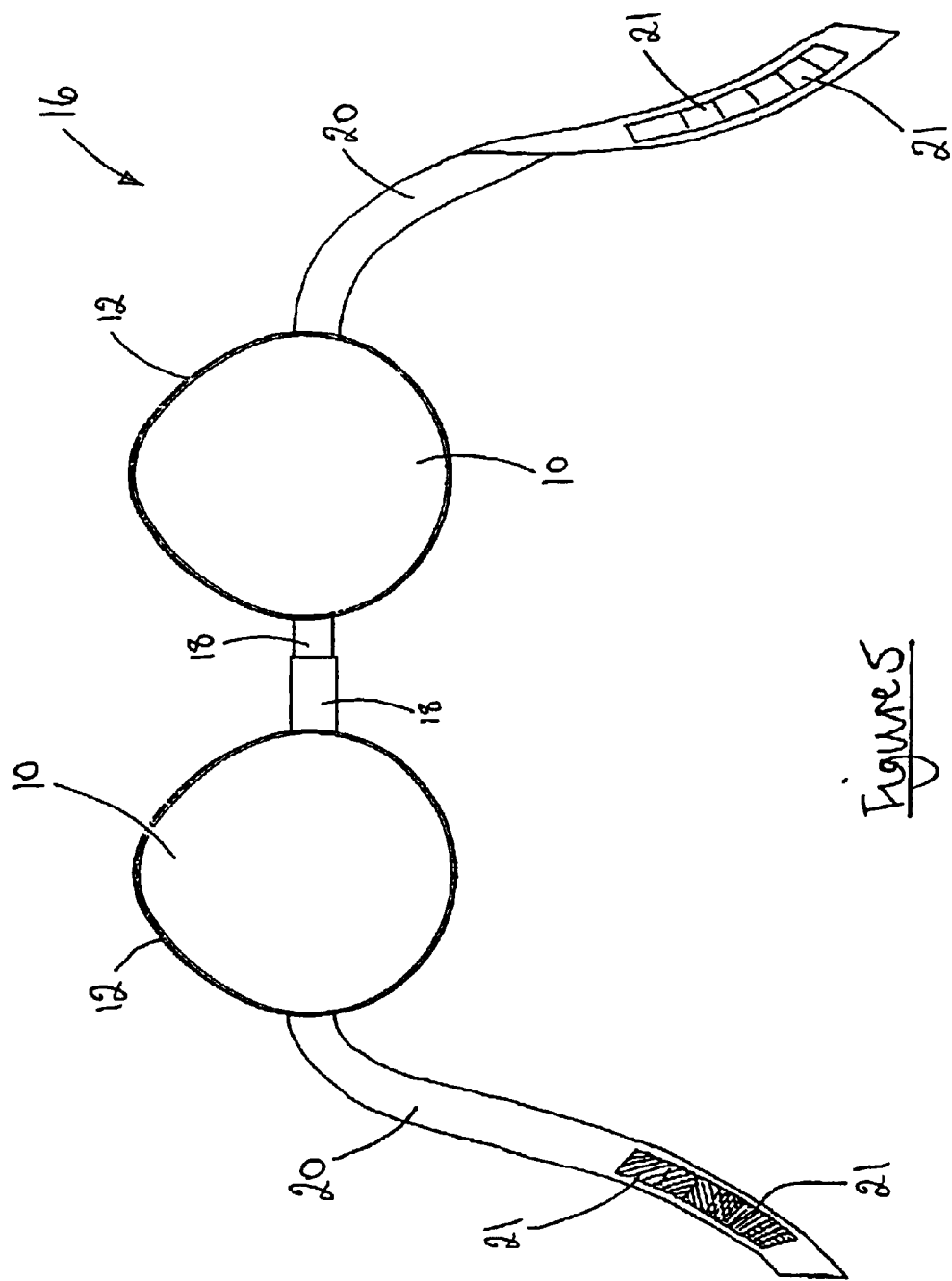
FIG. 5 shows two measuring receptacles as illustrated in FIGS. 2 to 4, fastened together to form a breast measuring device and including an optional, additional torso measuring strap.

When measuring breast volume, a single receptacle 10 may be used in turn on each breast. Alternatively, two receptacles 10 may be joined together to create a breast measuring device 16 emulating a bra as shown in FIG. 5. Two receptacles 10 may be attached to each other by flexible means 18 such as Velcro® or by lengths of tape or ribbon which may be tied or fixed together. These flexible means may also incorporate indicia (not shown) to measure the distance between the two breasts. While this measurement is less applicable to bras manufactured in relatively large quantities, it may provide an important measurement if a bra is to be tailored to the wearer.

An advantage of being able to attach one receptacle 10 to another is that a breast measuring device 16 may be assembled with two receptacles 10 of differing volumes to accommodate size differences between the breasts. Again, this will be more applicable to sizing breasts for a bra which is to be tailored to the wearer.

Additionally, each receptacle 10 may include flexible means that enable the breast measuring device to be held around the torso, suitably in the form of torso straps 20. These straps 20 constitute torso measurement means for assisting self-measurement of the wearer's torso. Where the measuring device 16 emulates a bra, as shown in FIG. 5, the torso measurement means 20 emulates the torso strap of a bra and therefore comprises two strap portions that fasten together.

The torso strap portions 20 may be of tape or ribbon, possibly including studs or Velcro®, and may or may not include measuring indicia 21. Where provided, such measuring indicia 21 may be characters, icons or a colour scale. However, it is helpful for the user if these indicia 21 are of a size that is readily visible so that the relevant indicia 21 can readily be understood when looking in a mirror, even over the shoulder if necessary.

It is almost impossible using a standard measuring tape to obtain an accurate measurement of torso size when peering behind oneself in a mirror, even when using an arrangement of two mirrors in which the reflected image from one mirror is viewed in the other mirror. Consequently, the readily-visible scale of the torso measuring means includes a series of indicia 21 that differ markedly from one another to the extent that the relative positions of the two strap portions, and hence the size of the wearer's torso, is readily apparent even when looking over the shoulder into a mirror.

For example, the indicia 21 could be a series of coloured regions, each colour corresponding to a particular torso size. It is further preferred that intermediate regions of the sequence are a combination of colours in the neighbouring blocks, e.g. red, red/blue stripes, blue.

It is notable in this respect that colour-based indicia 21 will work well whether viewed with one or two mirrors. Conversely, numerals or other characters would only work properly when viewed with two mirrors, because unless themselves expressed in mirror writing, numerals depend upon the mirror-image reversal of one mirror to be corrected by the other mirror.

Where the measuring device 16 emulates a bra as shown in FIG. 5, shoulder straps (not shown) may also be provided to help the wearer don the measuring device 16 by locating the receptacles 10 over the breasts while fastening the torso strap 20. Such straps suitably pass over each shoulder by extending between the top edge of each receptacle 10 and the torso measuring strap 20. To ensure a comfortable fit, the shoulder straps may also include means to adjust the length of each strap, for example, a simple sliding clasp.

Whilst over-shoulder measurement will not usually be necessary because shoulder straps of bras are generally capable of extensive length adjustment, it would be possible for similar measurement means as are proposed for the torso strap 20 to be applied to any shoulder straps that may be fitted to the measuring device 16.

Where torso straps 20 and/or shoulder straps form part of the measuring device 16, it is preferred that any fastenings are confined to the front or side of the user's torso. This ensures that the fastenings can be manipulated easily and that associated indicia 21 can be read directly, if necessary with the aid of a mirror situated conveniently in front or to one side of the user. If needs be, strap portions 20 can loop behind the wearer's back and cross over to extend back round to the front or side of the wearer's torso for fastening and measurement purposes.

Figure 6:
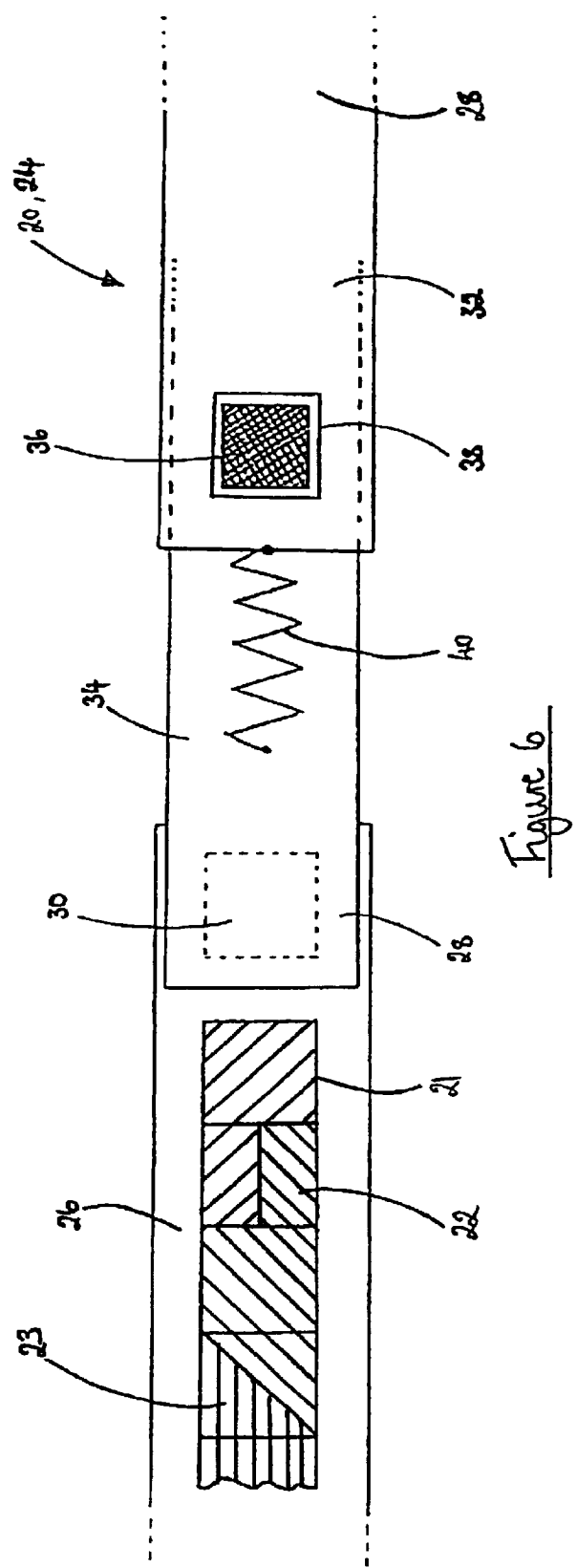
FIG. 6 is a detail plan view of a strap in accordance with the invention.

Referring now to FIG. 6 of the drawings, a strap according to the invention (which could be a torso strap 20 or a shoulder strap) comprises opposed first and second strap portions 26, 28 whose ends can be fastened together by Velcro® pads 28 when the ends are in overlapping relation as shown. As aforesaid, the strap portions 26, 28 have indicia 21, in this case a series of coloured rectangles disposed along the first strap portion 26, that can be read by a user to indicate the length of the fastened strap when a rectangle is aligned with the free end of the second strap portion 28.

FIG. 6 shows another technique for colouring an intermediate block among the indicia 21. This is to divide such a block into two regions, the colour of each region corresponding to the colour of each respective neighbouring block. This can be achieved in different ways, one way (shown by block 22 in FIG. 6) being to divide the block 22 into oblong halves divided by a longitudinal border and another way (shown by block 23 in FIG. 6) being to divide the block 23 into triangular halves divided by a diagonal border. An advantage of the latter arrangement is that the proportion of one colour to another exposed in use varies in accordance with the longitudinal relative positions of the strap portions 26, 28.

One of the strap portions 28 is itself divided into portions. These latter portions will be described as upper and lower portions 32, 34 in this instance because these portions too overlap, albeit in a manner that permits the upper portion 32 to slide over the lower portion 34. The lower portion 34 is marked with a rectangular indicator 36 and the upper portion is penetrated by a rectangular window 38 of similar size through which the whole of the indicator 36 can be viewed when the window 38 and the indicator 36 are aligned with each other. When the window 38 and the indicator 36 are slightly misaligned, only part of the indicator 36 is visible in the window 38 together with some neighbouring background of the lower portion 34. This indicates the direction of relative movement necessary to achieve proper alignment.

The free end of the upper portion 32 is linked to an intermediate part of the lower portion 34 by a spring 40 that transmits a tensile load from the upper portion 32 to the lower portion 34 when the second strap portion 28 is pulled taut. The spring 40 elongates under this load. The elongation characteristic of the spring 40 is selected so that when the load reaches a predetermined level corresponding to a tension within the second strap portion 28 that is deemed to be consistent with comfort, the indicator 36 is aligned with the window 38 to indicate this comfort point to the user. Accordingly, when the first and second strap portions 26, 28 have been fastened together under appropriate tension, the indicator 36 confirms that there is comfortable tension in the strap 20 as a whole.

In addition to ensuring comfort, the strap of FIG. 6 very simply provides consistency of girth measurement that is difficult to achieve when encircling a compressible body such as a torso. The problem is that pulling on a strap to ensure that it is taut compresses the body encircled by the strap, and so the girth of the body will change as a result of the measurement process. This introduces self-defeating inaccuracy unless a consistent degree of compression is created and allowed for.

It will be clear to those skilled in the art that the same principle can be applied to a measuring tape that is also within the ambit of the invention, and that an elastic band or other resilient bias means could be used in place of the spring.

In order for the measurement obtained by the user of the measuring device to be correlated with volumes of marketed bras, the invention contemplates means by which the size characteristics of any given bra can be measured accurately. Specifically, the invention contemplates a device including an artificial representation of a female torso as shown in FIGS. 7 and 8.

Figure 7:
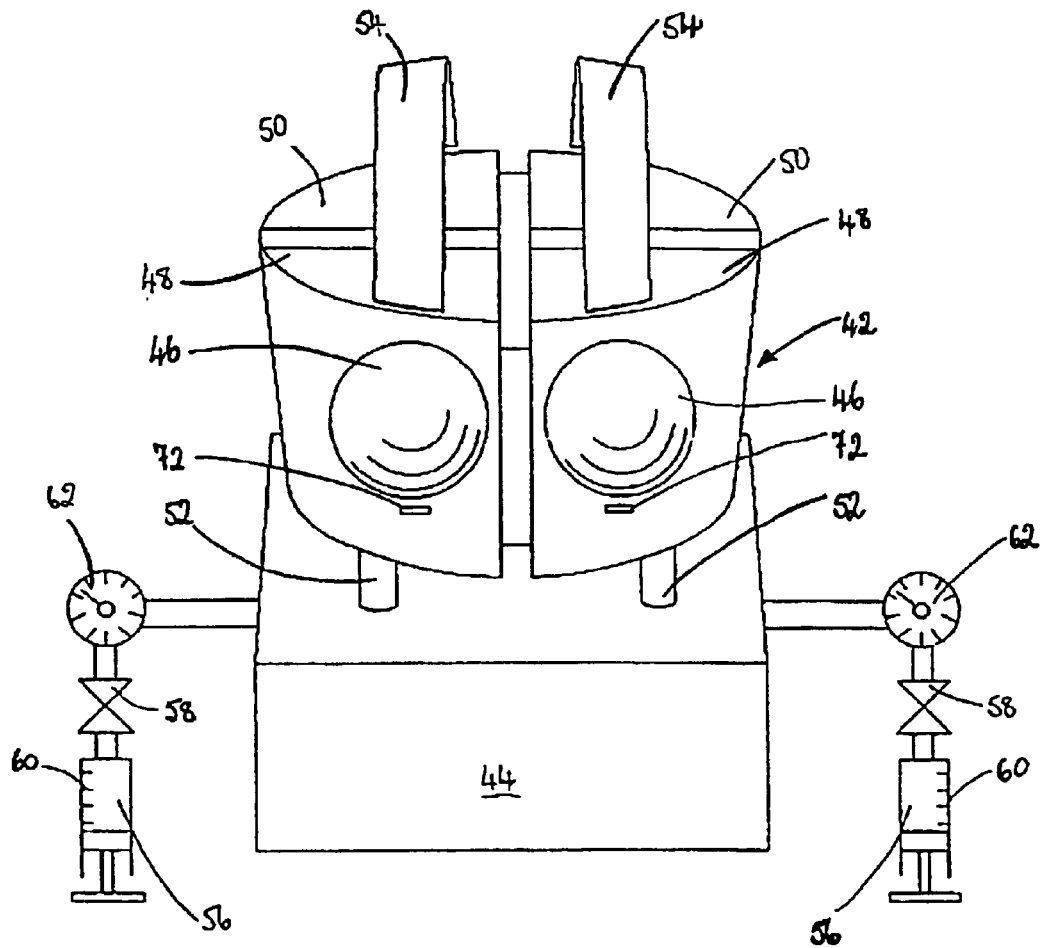
FIGS. 7 and 8 are schematic frontal perspective views of a bra measuring device in accordance with the invention.
Figure 8:
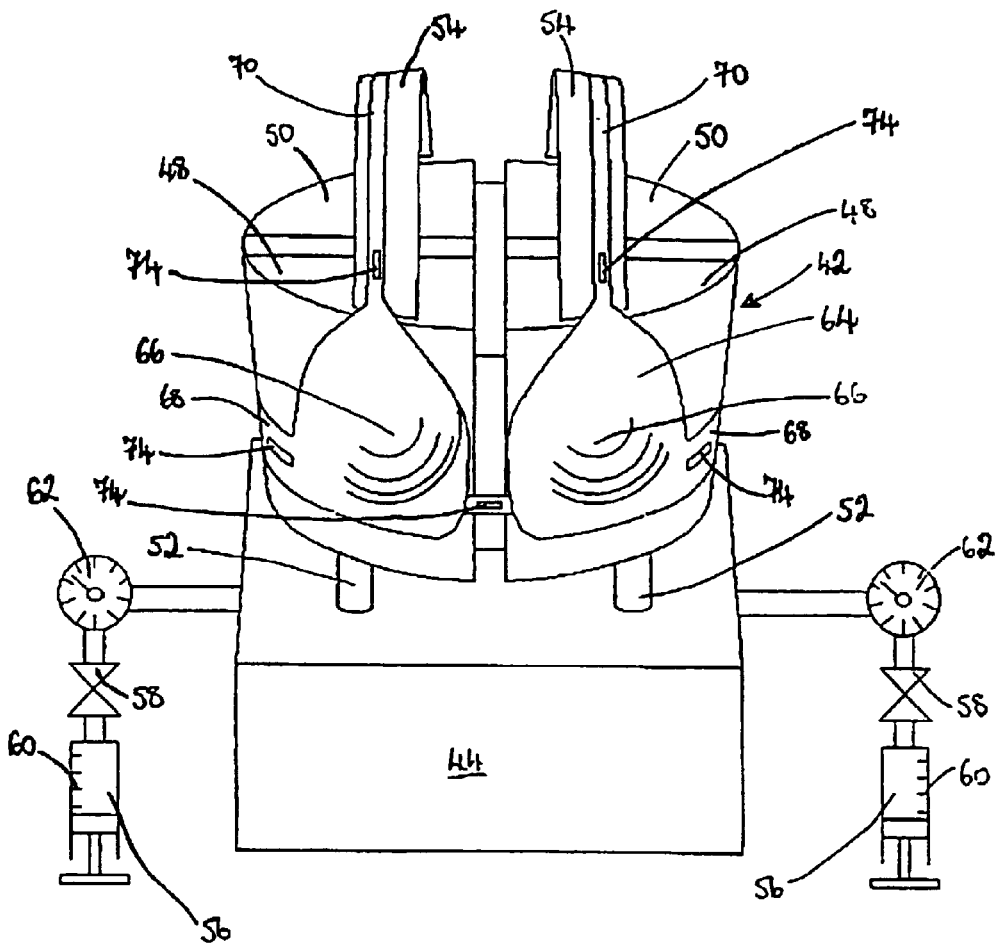

The artificial torso 42 in FIGS. 7 and 8 is generally elliptical in plan and is a frustum tapering downwardly towards a base 44 that supports the torso 42. The front of the artificial torso 42 includes at least one but preferably two bladders 46 of elastomeric material, the shape and positioning of which represent breasts.

To reduce the number of artificial torsos 42 necessary to measure a full range of bras, it is advantageous to include as many modes of adjustment as possible. For this reason, the artificial torso 42 is segmented in plan view into two frontal segments 48 and two rear segments 50 so that its girth can be varied by varying the separation of the segments 48, 50. Each segment 48, 50 is supported by a support leg 52 that is anchored by the base 44.

Arched shoulder supports 54 are an optional addition shown here extending from front to back over the segments 48, 50 of the artificial torso 42 to support shoulder straps of a bra. These shoulder supports 54 can be adjustable in height and separation to emulate long, short, wide and narrow torsos. Separation of the shoulder supports 54 can be adjusted by mounting them to segments 48, 50 whose separation is itself adjustable. It would also be possible to mount the shoulder supports 54 at different lateral positions with respect to their supporting segments 48, 50, thereby to emulate relatively wide-shouldered or narrow-shouldered women whose breast spacing is the same.

It will be noted that the respective bladders 46 are on separate frontal segments 48, this feature providing a means for varying the separation of the bladders 46 to emulate reality in which separation between breasts can vary. This also provides a means for varying the size or shape of the bladders 46 by interchangeably removing and replacing suitably-equipped frontal segments 48, thereby emulating different breast characteristics.

The separation between segments 48, 50 can be varied in many ways. For example, the segments 48, 50 can be mounted to respective carriages on the base 44, which carriages are movable with respect to the base 44 by propulsion means such as hydraulic rams, pneumatic actuators or stepper motors. Other ways of mounting the segments 48, 50 to the base 44 in a movable manner will be evident to those skilled in the art. For example, interchangeable segments 48, 50 can be differently offset with respect to their support legs 52 to vary the spacing between segments 48, 50. If desired, the segments 48, 50 need not be movable during a bra measurement operation, but only between such operations when it is desired to adapt the artificial torso 42 to emulate different torso girths.

Each bladder 46 is in communication with a respective pump 56, represented here schematically by a piston or plunger movable within a cylinder in the manner of a syringe. In reality, it is preferred that the pump 56 is a peristaltic pump having rotatable paddles such that the volume of fluid delivered can be inferred from the number of rotations of the paddles.

The pump 56 introduces a working fluid, preferably an incompressible and somewhat viscous liquid or (if compatible with the hydraulic system) a gel-like substance such as silicone, into the associated bladder 46 under pressure to expand the bladder 46 against the contracting force of the elastomeric material. A non-return valve 58 between each pump 56 and its associated bladder 46 retains pressure in the bladder 46 until that pressure is deliberately released.

Each pump 56 includes a volumetric scale 60 whereby the volume of fluid pumped in to the associated bladder 46 can be measured, thereby gaining an accurate indication of the volume of the bladder 46 at any point of the bladder expansion process. Pressure within each bladder 46 can be read off a respective pressure gauge 62 sited downstream of the associated non-return valve 58.

Whilst the duplicated pumps 56, non-return valves 58, volumetric scales 60 and pressure gauges 62 could conceivably be replaced by a single pump 56 and so on connected to both bladders by a common manifold, the duplicated arrangement is greatly preferred as it allows independent measurement of each bladder and compensates for variations between the bladders. Nevertheless, whilst shown externally for clarity, the pumps 56, non-return valves 58, volumetric scales 60 and pressure gauges 62 can all be housed in the base 44, with the volumetric scales 60 and pressure gauges 62 suitably being displayed on the front panel thereof. It is also emphasised that the syringe form of the pumps 56 is not essential, although it is currently much preferred for its accuracy in metering slow-flowing fluids.

In use when measuring the size characteristics of a bra 64 including, in particular, the volume of its cups 66, a bra 64 is fitted around the artificial torso 42 as shown in FIG. 8 and is located so that the partially-deflated bladders 46 fit inside the cups 66, with the torso straps of the bra 68 fitted around the artificial torso 42 and the shoulder straps 70, if any, passing over the shoulder supports 54. The pumps 56 are then activated to fill the bladders 46 with fluid, causing them to expand under internal fluid pressure until they occupy fully the cups 66 of the bra 64 being measured.

To gain a reasonably accurate indication of tightness and hence fit, the bra 64 and/or the artificial torso 42 can be fitted with various sensors to indicate tensile stress on the bra straps 68, 70 and/or cups 66, and pressure exerted on the torso 42 and/or the bladders 46 by the bra 64. These sensors include strain gauges and pressure sensors as appropriate, for example pressure sensors 72 on the artificial torso 42 immediately under the bladders 46 to determine pressure exerted by the bra 64 at the sensitive area where bras 64 are often stiffly reinforced by wires and cause the most discomfort if not properly fitted. These pressure sensors 72 are visible only in FIG. 7, being covered by the bra 64 shown in FIG. 8 which also includes strain gauges 74 associated with the torso strap 68 and the shoulder straps 70.

Using sensors such as these, the appropriate degree of expansion of the bladders 46 can be sensed, whereupon expansion can be stopped and the volume of the bladders 46 deduced from the amount of fluid that has been pumped in to them. It is also to be expected that when the bladders 46 have filled the bra cups 66 and their expansion is therefore restrained, continued operation of the pumps 56 will lead to sharply increasing pressure within the bladders 46. Early signs of this discontinuity observed on the pressure gauges 62 are a further indication that the bladders 46 are a comfortably close fit within the cups 66 of the bra 64 and that the pumps 56 should be stopped so that volumetric measurements of the bladders 46 should be taken. Control means may be provided automatically to stop the pumps 56 once the is discontinuity in the pressure curve is sensed.

These measurements can and should be supplemented by direct observation of fit, particularly to see when the cups 66 of the bra 64 are pushed away from the artificial torso 42 and when the straps 68, 70 of the bra 64 press against the supporting surfaces of the artificial torso 42, those supporting surfaces advantageously being of soft material emulating body tissue to enable easy visual recognition of localised compression at any pinch points. In general, it is preferred that the artificial torso 42 should be structured to emulate a rib cage, having a flexible and resilient layer of, for example, foam or rubber around a relatively rigid internal structure of, for example, metal that could be, but need not be, of skeletal form.

Figure 9:
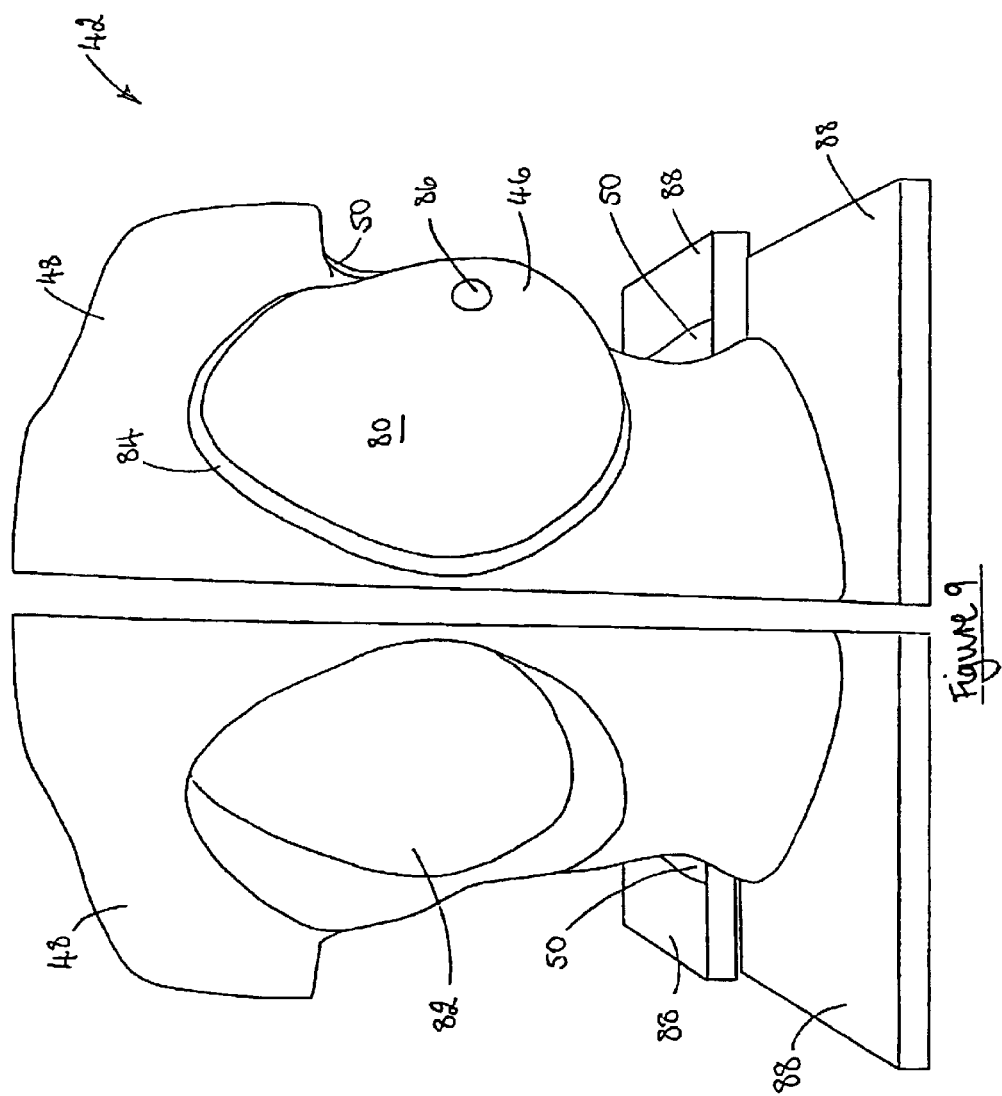
FIG. 9 is a front view of a prototype bra measuring device corresponding to the bra measuring device illustrated schematically in FIGS. 7 and 8.
Figure 10:
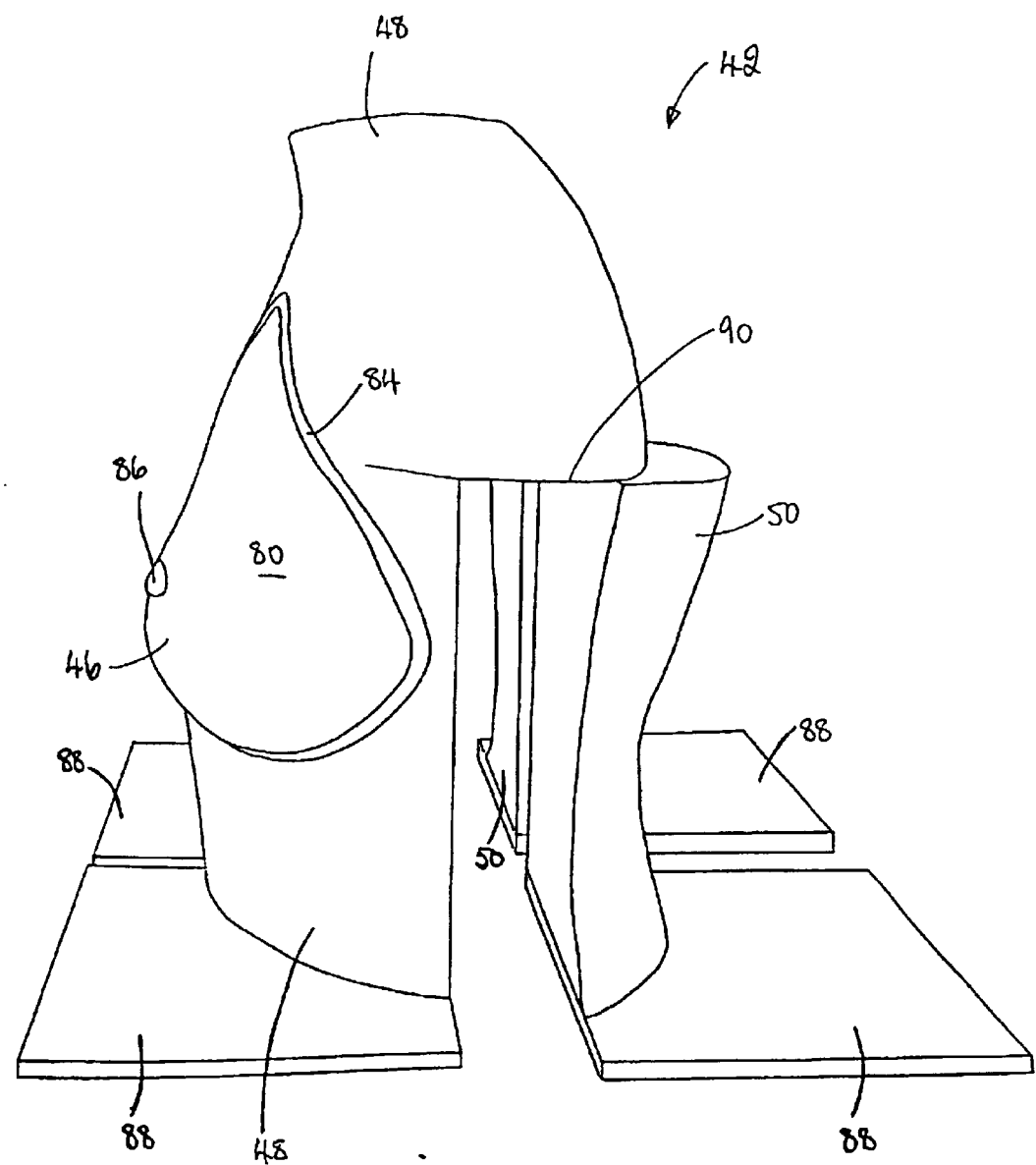
FIG. 10 is a side view of the prototype bra measuring device of FIG. 9.

Referring finally to FIGS. 9 and 10, a prototype bra measuring device broadly corresponds to the bra measuring device of FIGS. 7 and 8; like numerals are used for like parts, although details such as the pumps, gauges and associated pipework are omitted for clarity. It will be noted that the artificial torso 42 in FIGS. 9 and 10 more closely resembles a human female torso and that the front of the torso includes two removable elastomeric bladder modules 80, one of which has been removed in FIG. 9 to leave a recess 82 ready to accept a different bladder module 80 as needs be. Any suitable releasable fixing means (not shown) such as inter-engaging formations, bolts or clamps may be used to hold a bladder module 80 in place within its recess 82.

The bladder module 80 that remains in FIG. 9 shows how the bladder 46 is surrounded by a collar 84 shaped to fit the recess 82 and to support the bladder 46 in a breast-like shape, for which purpose the exposed front membrane of the bladder 46 is shaped to emulate a breast, being of half pear-shaped, half-teardrop or inverted semi-cardiod vertical cross section. A nipple formation 86 is also shown.

Whilst the bladder modules 80 will have identical mating features in terms of the overall shape and size of the collar 84 (save that some will be mirror-images of others to suit the two sides of the torso), the exposed front membrane of the bladder 46 will vary from module to module so as to emulate larger, smaller or differently-shaped breasts.

Again, the artificial torso 42 of FIGS. 9 and 10 is segmented in plan view into two frontal segments 48 and two rear segments 50 so that its girth can be varied by varying the separation of the segments 48, 50. In this instance, each segment 48, 50 is supported by a respective support plate 88 and each support plate 88 can be moved in relation to its neighbours by suitable means. Although not shown in the simplified views of FIGS. 9 and 10, it is envisaged that the support plates 88 can be moved on a system of threaded rods.

As best shown in the side view of FIG. 10, the optional arched shoulder supports 54 of FIGS. 7 and 8 are replaced by shoulder portions 90 integral with the front segments 48 that extend rearwardly over the rear segments 50 to support the shoulder straps of a bra (not shown).

The artificial torsos 42 exemplified by FIGS. 7 to 10 may have a further advantageous feature to emulate the correct way in which a wearer having relatively large breasts should don a bra. Specifically, the torso 42 can be mounted on a tiltable support in which, for example, a hydraulic ram can be actuated to pivot the torso forwards through about 90° about a horizontal pivot axis. This causes the bladders 46 representing breasts to hang down, whereupon a bra 68 can be lifted onto the bladders 46 and secured about the torso 42. Of course, the bra 68 can be partially or fully secured about the torso 42 before tilting takes place, the tilting then merely assisting correct fitting of the bladders 46 within the cups of the bra 68.

Those skilled in the art will know that the present invention may be embodied in other specific forms without departing from its spirit or essential attributes. For example, bladders of the bra measuring device could be interchangeably mounted to to the segments that make up the artificial torso. Also, a further bladder could be associated with the artificial torso and/or its segments to vary torso girth during bra measurement thereby to assess the effect of different torso sizes on bra fit. A similar effect could be obtained by moving the segments of the artificial torso during bra measurement to vary their mutual separation.

In view of these and other variants, reference should be made to the appended claims and other general or conceptual statements herein rather than to the foregoing specific description as indicating the scope of the invention.

What is claimed is:

1. A breast measuring method comprising the steps of:
providing a receptacle of known volume, the receptacle being pre-formed to be substantially of pear-shaped, teardrop, or cardioid vertical cross section emulating the shape of a bra-supported breast and being sufficiently rigid to be self-supporting and to support the breast in the shape of the receptacle, said receptacle being configured to contain the breast therein;
applying the receptacle to a breast to determine the volume of the breast when the breast is comfortably fitted within and supported by the receptacle:
and checking fit by observing the breast through the receptacle.

2. The method of claim 1, further comprising applying in turn to a breast a plurality of receptacles of different volumes and/or shapes and selecting from that plurality the receptacle giving the most comfortable supporting fit to the breast received within.

3. The method of claim 2, further comprising identifying the volume and/or shape of the selected receptacle.

4. The method of claim 3, further comprising reading the volume or shape of the selected receptacle from indicia applied to the receptacle.

5. The method of claim 1, wherein the checking fit step comprises checking fit by observing contact of the breast with the receptacle.

6. The method of claim 1, wherein the checking fit step comprises checking fit by checking for a gap between the receptacle and the torso around the breast.

7. The method of claim 1, wherein the checking fit step comprises checking fit by feeling for pressure of the receptacle on the breast.

8. The method of claim 1, wherein the step of applying the receptacle comprises holding the receptacle on the user's breast by a hand.

9. The method of claim 1, wherein the step of applying the receptacle is first performed on one breast and then on the other breast.

10. The method of claim 1, further comprising the step of providing a second receptacle and wherein the step of applying the receptacle comprises applying one receptacle to one breast and the second receptacle to the other breast so that receptacles are applied on both breasts simultaneously.

11. The method of claim 10, further comprising linking two receptacles and applying them together to the respective breasts.

12. The method of claim 11, further comprising measuring separation of the breasts.

13. The method of claim 1, further comprising the step of performing the method at home or otherwise remote from a retail stock of bras.

14. The method of claim 1, wherein the or each pre-formed receptacle can be stored in a flattened state before use and wherein the method further comprises reforming the or each receptacle from the flattened state to ready the or each receptacle for use.

15. The method of claim 1, further comprising measuring torso girth.

16. The method of claim 15, wherein the step of measuring torso girth comprises passing a tape or strap around the torso and reading a girth measurement from indicia on the tape or strap situated at the front or side of the torso.

17. The method of claim 16, wherein the step of measuring torso girth comprises applying a predetermined tensile load to the tape or strap before reading the girth measurement.

18. A breast measuring apparatus comprising a receptacle of known volume applicable to a breast to check for comfortable fit and to determine the volume of the breast comfortably fitted within the receptacle, the receptacle being pre-formed to be substantially of pear-shaped, teardrop or cardioid vertical section emulating the shape of a bra-supported breast and being sufficiently rigid to be self-supporting and to support the breast in the shape of the receptacle, a wall of the receptacle being transparent or translucent to enable fit to be checked by observing the breast through the receptacle and configured to contain the breast therein.

19. The apparatus of claim 18, wherein a wall of the receptacle has a textured external surface portion.

20. The apparatus of claim 19, wherein the textured external surface portion delineates a viewing region of transparent or translucent material.

21. The apparatus of claim 20, wherein the viewing region encompasses a central apical region of the wall.

22. The apparatus of claim 21, wherein the textured external surface portion is a loop.

23. The apparatus of claim 22, wherein the loop is waisted to define upper and lower portions connected by a narrow neck.

24. The apparatus of claim 20, wherein the viewing region encompasses a peripheral region of the wall.

25. The apparatus of claim 18, wherein a rim of the receptacle is reinforced.

26. The apparatus of claim 25, wherein the rim is defined by a rolled or thickened edge.

27. The apparatus of claim 18, and further comprising a plurality of receptacles.

28. The apparatus of claim 27, further comprising a set of receptacles of different volumes and/or shapes.

29. The apparatus of claim 28, wherein each receptacle of the set includes indicia indicating its volume and/or shape.

30. The apparatus of claim 28, wherein receptacles of the set are nestable within one another.

31. The apparatus of claim 18, wherein a pair of receptacles are linked to emulate a bra.

32. The apparatus of claim 31, further including a torso strap.

33. The apparatus of claim 32, wherein the torso strap includes strap portions fastenable at the front or side of a wearer's torso.

34. The apparatus of claim 32, wherein the torso strap includes indicia for indicating torso girth.

35. The apparatus of claim 34, wherein the indicia comprises a series of coloured regions disposed successively along the torso strap.

36. The apparatus of claim 35, wherein an intermediate coloured region mixes colours of neighbouring regions.

37. The apparatus of claim 32, wherein the torso strap includes load indicator means for indicating when a predetermined tensile load has been applied to the strap.

38. The apparatus of claim 32, further including shoulder straps.

* * * * *